US012649602B2

(12) United States Patent
Vetter et al.

(10) Patent No.: US 12,649,602 B2
(45) Date of Patent: Jun. 9, 2026

(54) METHOD AND MANUFACTURING DEVICE FOR STERILISING AN INTERIOR OF A PACKAGING, AND PACKAGING WITH STERILISED INTERIOR

(71) Applicant: Vetter Pharma-Fertigung GmbH & Co. KG, Ravensburg (DE)

(72) Inventors: Michael Vetter, Ravensburg (DE); Dieter Ertel, Ummendorf (DE); Claudia Roth, Bad Saulgau (DE); Anthony Richard Blencowe, Adelaide (AU)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 308 days.

(21) Appl. No.: 18/268,995

(22) PCT Filed: Dec. 20, 2021

(86) PCT No.: PCT/EP2021/086896
§ 371 (c)(1),
(2) Date: Jun. 22, 2023

(87) PCT Pub. No.: WO2022/136322
PCT Pub. Date: Jun. 30, 2022

(65) Prior Publication Data
US 2024/0059445 A1 Feb. 22, 2024

(30) Foreign Application Priority Data
Dec. 22, 2020 (DE) .......................... 102020216516.5

(51) Int. Cl.
*B65B 55/18* (2006.01)
*A61B 50/30* (2016.01)
(Continued)

(52) U.S. Cl.
CPC ................ *B65B 55/18* (2013.01); *A61L 2/16* (2013.01); *B65B 55/103* (2013.01); *A61B 50/30* (2016.02); *A61B 50/33* (2016.02)

(58) Field of Classification Search
CPC .......... B65B 55/103; B65B 55/18; A61L 2/16
(Continued)

(56) References Cited

U.S. PATENT DOCUMENTS 3,086,336 A * 4/1963 Rausing .................. B65B 55/04
493/212
3,235,446 A * 2/1966 Shelanski .................. C08J 9/40
510/438
(Continued)

FOREIGN PATENT DOCUMENTS

DE 732491 C 3/1943
DE 2135476 A1 1/1973
(Continued)

OTHER PUBLICATIONS

International Search Report issued in corresponding International Application No. PCT/EP2021/086896, dated Apr. 26, 2022, pp. 1-2, English Translation.
(Continued)

*Primary Examiner* — Joshua G Kotis
(74) *Attorney, Agent, or Firm* — Carter, DeLuca & Farrell LLP; George Likourezos

(57) ABSTRACT
The invention relates to a method for sterilising an interior of a packaging, wherein
the packaging has an upper film and a lower part, wherein
the upper film and the lower part, in the closed state of the packaging, delimit the interior at least in some regions, wherein
a sterilising substance is applied to a first surface of the upper film, wherein
(Continued)

Figure 1:
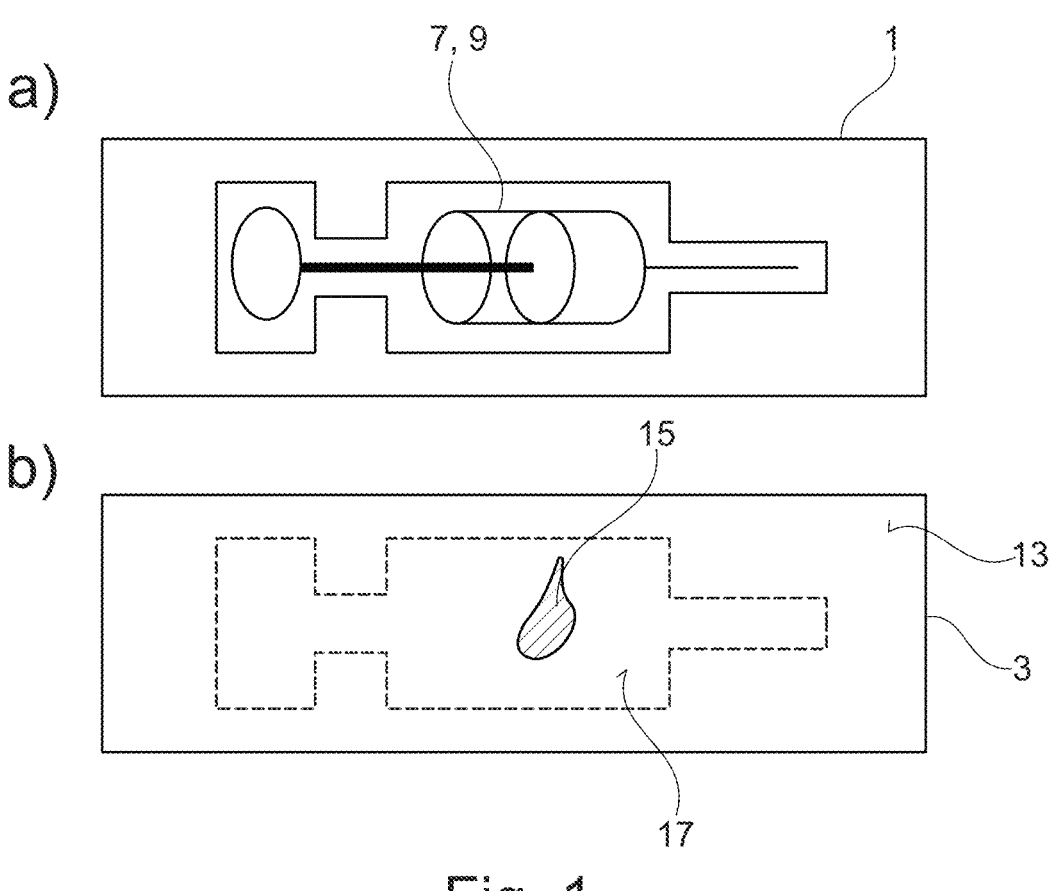

the sterilising substance contains iodine, wherein
the upper film is arranged on the lower part in such a way
    that the first surface of the upper film faces the interior
    of the packaging at least in some regions, wherein
the sterilising substance is arranged within the packaging
    and is activated from outside for a predetermined
    activation time period, and wherein
an initial germ load within the packaging, in particular in
    the interior of the packaging, is preferably reduced by
    a factor of at least $10^6$.

22 Claims, 2 Drawing Sheets

(51) Int. Cl.
    *A61L 2/16*        (2006.01)
    *B65B 55/10*       (2006.01)
    *A61B 50/33*       (2016.01)
(58) Field of Classification Search
    USPC ......................................................... 53/425
    See application file for complete search history.

(56)                 References Cited

U.S. PATENT DOCUMENTS

| | | | | |
|---|---|---|---|---|
| 3,618,283 | A | | 11/1971 | Moore et al. |
| 3,725,003 | A | * | 4/1973 | Moore .................... B65B 55/14 |
| | | | | 422/38 |
| 3,754,368 | A | * | 8/1973 | Moore .................... B65B 55/14 |
| | | | | 53/425 |
| 3,857,677 | A | * | 12/1974 | Moore .................... A23B 2/00 |
| | | | | 53/425 |
| 3,938,659 | A | * | 2/1976 | Wardwell ........... B65D 75/5855 |
| | | | | 53/433 |
| 4,381,380 | A | | 4/1983 | Leveen |
| 4,482,053 | A | * | 11/1984 | Alpern ...................... A61L 2/26 |
| | | | | 206/439 |
| 4,663,122 | A | * | 5/1987 | Sparks ...................... A61L 2/07 |
| | | | | 422/26 |
| 5,345,746 | A | * | 9/1994 | Franchi ................... B65B 55/14 |
| | | | | 53/425 |
| 10,245,025 | B2 | | 4/2019 | Prikril |
| 2004/0220614 | A1 | * | 11/2004 | Scalzo ............. A61B 17/06114 |
| | | | | 606/228 |
| 2005/0160701 | A1 | * | 7/2005 | Stevens ..................... A61L 2/08 |
| | | | | 435/284.1 |
| 2005/0173270 | A1 | | 8/2005 | Bourne |
| 2010/0107570 | A1 | * | 5/2010 | Khan ...................... B65B 5/103 |
| | | | | 53/370.7 |
| 2010/0163435 | A1 | | 7/2010 | Fischer et al. |
| 2012/0199502 | A1 | * | 8/2012 | Scalzo .................. A61L 17/005 |
| | | | | 53/425 |
| 2012/0282323 | A1 | | 11/2012 | Muehlau |
| 2013/0205717 | A1 | * | 8/2013 | Bowden ................. A23B 2/708 |
| | | | | 53/403 |
| 2013/0264226 | A1 | | 10/2013 | Prikril et al. |
| 2014/0215976 | A1 | | 8/2014 | Maasarani |
| 2015/0114855 | A1 | * | 4/2015 | Glick ...................... B65D 81/18 |
| | | | | 206/5 |
| 2015/0374729 | A1 | * | 12/2015 | Glauber ............... A61K 31/045 |
| | | | | 206/572 |
| 2017/0105877 | A1 | * | 4/2017 | Buteux ................. A61F 13/068 |
| 2018/0064835 | A1 | * | 3/2018 | Young .................... B65B 55/18 |
| 2018/0272019 | A1 | | 9/2018 | Roberts |
| 2019/0000579 | A1 | * | 1/2019 | Llinas .................... A61B 46/20 |
| 2020/0399005 | A1 | * | 12/2020 | Mullins ............... B65D 83/765 |
| 2022/0354635 | A1 | * | 11/2022 | Dockhorn ............. A61B 50/20 |

FOREIGN PATENT DOCUMENTS

| | | | |
|---|---|---|---|
| JP | 2015515324 | A | 5/2015 |
| JP | 2015530128 | A | 10/2015 |
| JP | 2017536310 | A | 12/2017 |
| RU | 2546289 | C2 | 4/2015 |
| WO | 2013152271 | A1 | 10/2013 |
| WO | 2014014728 | A1 | 1/2014 |
| WO | 2016069864 | A2 | 5/2016 |

OTHER PUBLICATIONS

Russian Office Action issued by the Russian Patent Office in
connection with International Application No. 2023119146, dated
Oct. 25, 2024.
International Preliminary Report on Patentability issued by the
International Bureau of WIPO in connection with International
Application No. PCT/EP2021/086896, dated Jun. 13, 2023.
Japanese Office Action issued by the Japanese Patent Office in
connection with International Application No. 2023537483, dated
Mar. 11, 2025. (Translated).

* cited by examiner a)

7, 9

1 b)

15

13

3

17

10

11

13

3

5

1

7, 9

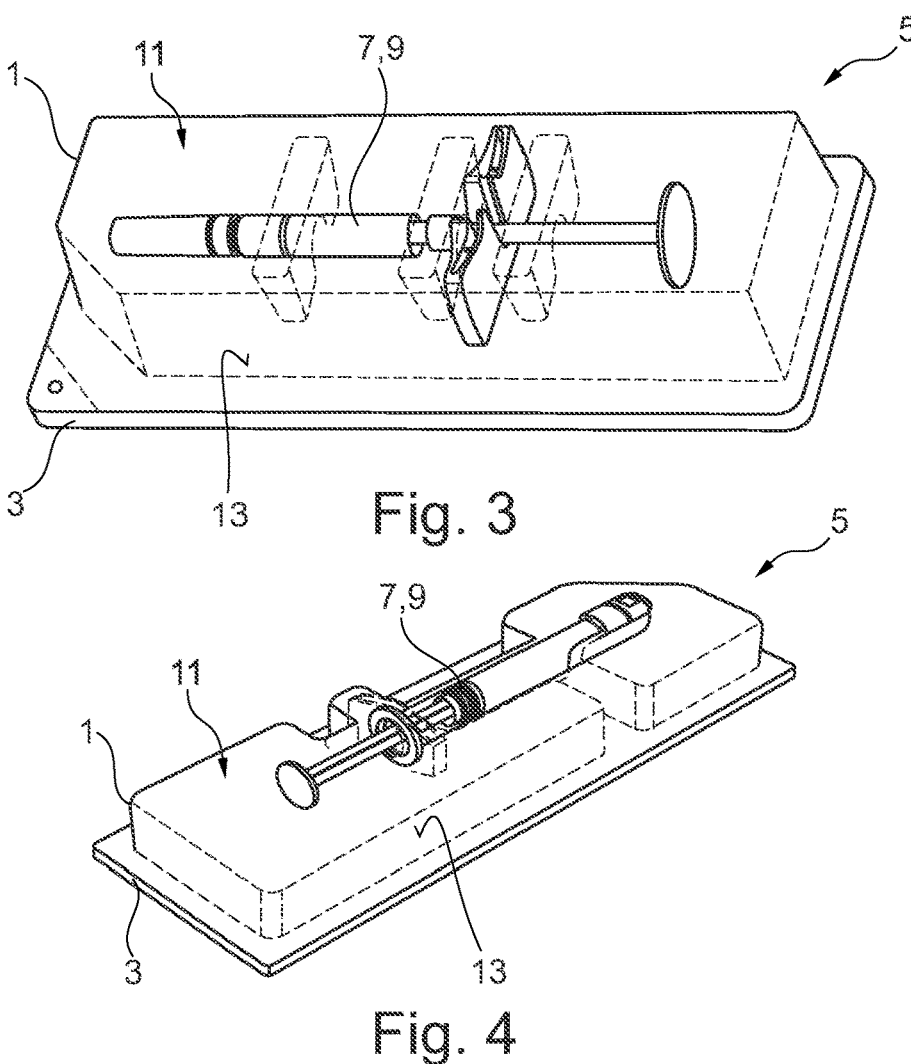
Fig. 3
Fig. 4
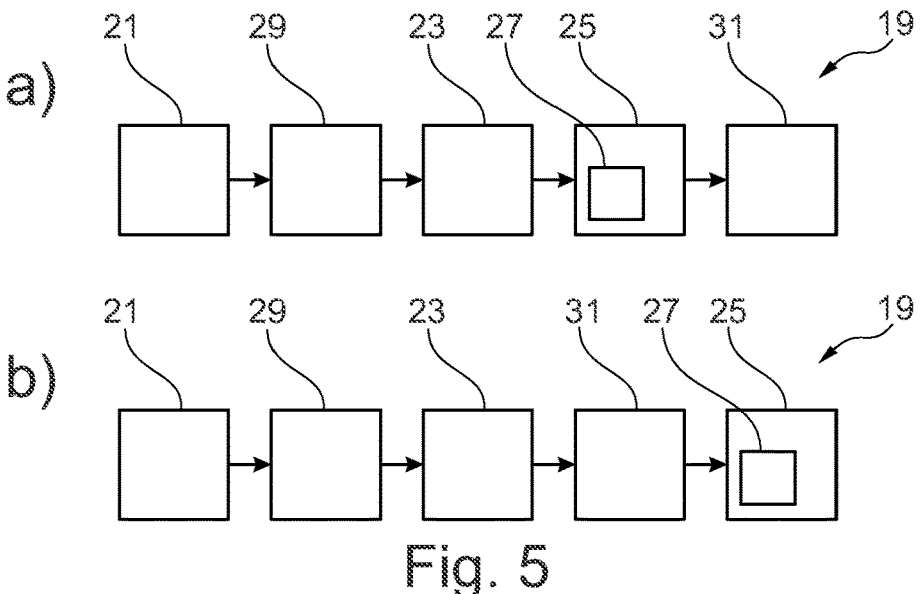
a)
b)
Fig. 5

METHOD AND MANUFACTURING DEVICE FOR STERILISING AN INTERIOR OF A PACKAGING, AND PACKAGING WITH STERILISED INTERIOR

CROSS REFERENCE TO RELATED APPLICATIONS

The present application is a national stage application of International Application No. PCT/EP2021/086896, filed Dec. 20, 2021, which claims priority to German Patent Application No. 102020216516.5, filed Dec. 22, 2020, the entire contents of which are incorporated herein by reference in their entirety.

The invention relates to a method for sterilising an interior of a packaging, a packaging with an interior sterilised according to such a method, and a manufacturing device for sterilising an interior of a packaging.

Ethylene oxide sterilisation is known for sterilising an interior of a packaging, in particular of a filled medical or pharmaceutical primary packaging means arranged within a packaging. Such an ethylene oxide sterilisation is procedurally complex and cost-intensive and is typically carried out exclusively by specialised service providers. The disadvantage of this is an increased complexity and a limited choice of the primary packaging material.

The U.S. Pat. No. 4,381,380 A describes a thermoplastic material made of polyurethane comprising iodine compounds. Comprising iodine compounds, the plastic has an antibacterial effect, in particular a sterilising effect. The disadvantage of this is the complex synthesis of polyurethane with iodine compounds and the restriction to polyurethane as a plastic.

The US patent US 2005/173 270 A1 describes a packaging for medical devices with an antimicrobial effect. The antimicrobial effect is achieved by adding an antimicrobial agent, in particular iodine. A disadvantage of this method is that sterilisation is not guaranteed.

The invention is therefore based on the problem of providing a method and a device for sterilising an interior of a packaging as well as a packaging with a correspondingly sterilised interior, wherein the disadvantages mentioned are at least partially eliminated, preferably avoided.

The problem is solved by providing the present technical teaching, in particular the teaching of the independent claims as well as the embodiments disclosed in the dependent claims and the description.

The problem is solved in particular by providing a method for sterilising an interior of a packaging, wherein the packaging comprises an upper film and a lower part and the upper film and the lower part, in the closed state of the packaging, delimit the interior at least in regions. In a first step, a sterilising substance is applied to a first surface of the upper film, wherein the sterilising substance comprises iodine. In a second step, the upper film is arranged on the lower part in such a way that the first surface of the upper film faces the interior at least in certain regions. In a third step, the sterilising substance, which is arranged inside the packaging, is activated from the outside for a predetermined activation time period.

Advantageously, the activation of the sterilising substance, in particular iodine, causes the interior of the packaging to be sterilised and, in particular, causes external sterilisation to be carried out on all the products arranged in the interior of the packaging. In addition, the sterilisation of the interior of the packaging by means of the sterilising substance, in particular iodine, and an activation of the sterilising substance, in particular iodine, is advantageously easy to integrate into existing processes and/or methods.

Particularly preferably, a film, in particular a plastic film, or a moulded part, in particular a plastic moulded part, is used as the lower part.

Preferably, the activation of the sterilising substance corresponds to a kinetic activation. Particularly preferably, the activation of the sterilising substance corresponds to a release of iodine from a solution.

Preferably, the sterilising substance is a compound, in particular a chemical compound, comprising iodine. Alternatively, the sterilising substance is particularly preferably a mixture of substances comprising iodine.

Preferably, the predetermined activation time period is from at least 0.1 seconds to at most 300 seconds, more preferably from at least 0.2 seconds to less than 60 seconds. Particularly preferably, the predetermined activation time period is at most 55 seconds. Particularly preferably, the predetermined activation time period is at most 50 seconds. Particularly preferably, the predetermined activation time period is at most 45 seconds. Particularly preferably, the predetermined activation time period is at most 40 seconds. Particularly preferably, the predetermined activation time period is at most 35 seconds. Particularly preferably, the predetermined activation time period is at most 30 seconds. Particularly preferably, the predetermined activation time period is at most 25 seconds. Particularly preferably, the predetermined activation time period is at most 20 seconds. Particularly preferably, the predetermined activation time period is at most 15 seconds. Particularly preferably, the predetermined activation time period is at most 10 seconds. Particularly preferably, the predetermined activation time period is at most 9 seconds. Particularly preferably, the predetermined activation time period is at most 8 seconds. Particularly preferably, the predetermined activation time period is at most 7 seconds. Particularly preferably, the predetermined activation time period is at most 6 seconds. Particularly preferably, the predetermined activation time period is at most 5 seconds. Particularly preferably, the predetermined activation time period is at least 0.5 seconds. Particularly preferably, the predetermined activation time period is at least 1 second. Particularly preferably, the predetermined activation time period is at least 1.5 seconds. Particularly preferably, the predetermined activation time period is at least 2 seconds. Particularly preferably, the predetermined activation time period is at least 2.5 seconds. Particularly preferably, the predetermined activation time period is at least 3 seconds. Particularly preferably, the predetermined activation time period is at least 3.5 seconds. Particularly preferably, the predetermined activation time period is at least 4 seconds. Particularly preferably, the predetermined activation time period is at least 4.5 seconds. Particularly preferably, the predetermined activation time period is at least 5 seconds. Particularly preferably, the predetermined activation time period is 5 seconds.

Preferably, the amount of sterilising substance applied to the first surface of the upper film is such that at least 0.001 mg iodine per cm 2 to at most 10 mg iodine per cm 2 is present on the first surface of the upper film. Alternatively or additionally, the sterilising substance preferably comprises at least 0.01 mg iodine per ml to at most 5 mg iodine per ml.

Preferably, the sterilising substance comprises more than 30 wt % iodine. Particularly preferably, the sterilising substance comprises at least 31 wt % iodine. Particularly preferably, the sterilising substance comprises at least 32 wt % iodine. Particularly preferably, the sterilising substance comprises at least 33 wt % iodine. Particularly preferably, the sterilising substance comprises at least 34 wt % iodine. Particularly preferably, the sterilising substance comprises at least 35 wt % iodine. Particularly preferably, the sterilising substance comprises at least 36 wt % iodine. Particularly preferably, the sterilising substance comprises at least 37 wt % iodine. Particularly preferably, the sterilising substance comprises at least 38 wt % iodine. Particularly preferably, the sterilising substance comprises at least 39 wt % iodine. Particularly preferably, the sterilising substance comprises at least 40 wt % iodine. Particularly preferably, the sterilising substance comprises at least 41 wt % iodine. Particularly preferably, the sterilising substance comprises at least 42 wt % iodine. Particularly preferably, the sterilising substance comprises at least 43 wt % iodine. Particularly preferably, the sterilising substance comprises at least 44 wt % iodine. Particularly preferably, the sterilising substance comprises at least 45 wt % iodine. Preferably, the sterilising substance comprises at most 50 wt % iodine, preferably at most 49 wt %, preferably at most 48 wt %, preferably at most 47 wt %, preferably at most 46 wt %.

The quantity wt % is a designation for mass percentage and in particular for a mass fraction.

According to a further development of the invention, it is provided that the sterilising substance comprises at least 40 wt % iodine.

According to a further development of the invention, it is provided that the sterilising substance is dried for a predetermined drying time period after application to the first surface of the upper film. Advantageously, this ensures an optimal coating of the sterilising substance on the first surface of the upper film.

Preferably, the predetermined drying time period is from at least 5 seconds to at most 10 minutes. Particularly preferably, the predetermined drying time period is at least 10 seconds. Particularly preferably, the predetermined drying time period is at least 15 seconds. Particularly preferably, the predetermined drying time period is at least 20 seconds. Particularly preferably, the predetermined drying time period is at least 25 seconds. Particularly preferably, the predetermined drying time period is at most 5 minutes. Particularly preferably, the predetermined drying time period is at most 2 minutes. Particularly preferably, the predetermined drying time period is at most 1 minute.

According to a further development of the invention, it is provided that the sterilising substance is applied as a layer, in particular as a homogeneous layer, to the first surface of the upper film. Advantageously, a layer, in particular a homogeneous layer, of the sterilising substance can be optimally activated from the outside.

According to a further development of the invention, it is provided that the upper film and the lower part are firmly bonded to each other. Preferably, the firmly bonded compound between the upper film and the lower part is configured by means of bonding or welding. Advantageously, the firmly bonded compound of the upper film to the lower part ensures that no fluid can escape from the interior of the packaging between the upper film and the lower part.

Preferably, the packaging is closed—in particular tightly and/or firmly—by producing the firmly bonded compound between the upper film and the lower part.

According to a further development of the invention, it is provided that the sterilising substance is activated before and/or after the packaging is closed.

According to a further development of the invention, it is provided that the activation is carried out by evaporating with a predetermined activation temperature and/or a predetermined activation pressure for the predetermined activation time period.

Preferably, the predetermined activation temperature is at least 60° C. to at most 250° C., more preferably at least 100° C. and less than 200° C. Particularly preferably, the predetermined activation temperature is at most 195° C. Particularly preferably, the predetermined activation temperature is at most 190° C. Particularly preferably, the predetermined activation temperature is at most 185° C. Particularly preferably, the predetermined activation temperature is at most 180° C. Particularly preferably, the predetermined activation temperature is at most 175° C. Particularly preferably, the predetermined activation temperature is at most 170° C. Particularly preferably, the predetermined activation temperature is at most 165° C. Particularly preferably, the predetermined activation temperature is at most 160° C. Particularly preferably, the predetermined activation temperature is at most 155° C. Particularly preferably, the predetermined activation temperature is at most 150° C. Particularly preferably, the predetermined activation temperature is at most 145° C. Particularly preferably, the predetermined activation temperature is at most 140° C. Particularly preferably, the predetermined activation temperature is at most 135° C. Particularly preferably, the predetermined activation temperature is at most 130° C. Particularly preferably, the predetermined activation temperature is at most 125° C. Particularly preferably, the predetermined activation temperature is at most 120° C. Particularly preferably, the predetermined activation temperature is at least 65° C. Particularly preferably, the predetermined activation temperature is at least 70° C. Particularly preferably, the predetermined activation temperature is at least 75° C. Particularly preferably, the predetermined activation temperature is at least 80° C. Particularly preferably, the predetermined activation temperature is at least 85° C. Particularly preferably, the predetermined activation temperature is at least 90° C. Particularly preferably, the predetermined activation temperature is at least 95° C. Particularly preferably, the predetermined activation temperature is at least 105° C. Particularly preferably, the predetermined activation temperature is at least 110° C. Particularly preferably, the predetermined activation temperature is at least 115° C. Particularly preferably, the predetermined activation temperature is at least 120° C. Particularly preferably, the predetermined activation temperature is 120° C.

Preferably, the predetermined activation pressure is at least 1 psi (0.069 bar) to at most 350 psi (24 bar), more preferably at least 30 psi (2.1 bar) to at most 340 bar. Particularly preferably, the predetermined activation pressure is at most 320 psi (22 bar). Particularly preferably, the predetermined activation pressure is at most 300 psi (21 bar). Particularly preferably, the predetermined activation pressure is at most 280 psi (19 bar). Particularly preferably, the predetermined activation pressure is at most 260 psi (18 bar). Particularly preferably, the predetermined activation pressure is at most 240 psi (17 bar). Particularly preferably, the predetermined activation pressure is at most 220 psi (15 bar). Particularly preferably, the predetermined activation pressure is at most 200 psi (14 bar). Particularly preferably, the predetermined activation pressure is at most 180 psi (12 bar). Particularly preferably, the predetermined activation pressure is at most 160 psi (11 bar). Particularly preferably, the predetermined activation pressure is at most 140 psi (9.7 bar). Particularly preferably, the predetermined activation pressure is at most 120 psi (8.3 bar). Particularly preferably, the predetermined activation pressure is at most 100 psi (6.9 bar). Particularly preferably, the predetermined activation pressure is at least 2 psi (0.14 bar). Particularly preferably, the predetermined activation pressure is at least 3 psi (0.21 bar). Particularly preferably, the predetermined activation pressure is at least 4 psi (0.28 bar). Particularly preferably, the predetermined activation pressure is at least 5 psi (0.34 bar). Particularly preferably, the predetermined activation pressure is at least 6 psi (0.41 bar). Particularly preferably, the predetermined activation pressure is at least 7 psi (0.48 bar). Particularly preferably, the predetermined activation pressure is at least 8 psi (0.55 bar). Particularly preferably, the predetermined activation pressure is at least 9 psi (0.62 bar). Particularly preferably, the predetermined activation pressure is at least 10 psi (0.69 bar). Particularly preferably, the predetermined activation pressure is at least 15 psi (1.03 bar). Particularly preferably, the predetermined activation pressure is at least 20 psi (1.4 bar). Particularly preferably, the predetermined activation pressure is at least 25 psi (1.7 bar).

In a preferred embodiment of the method, the evaporation is carried out by means of a steam nozzle which is applied directly to the upper film or is arranged at a predetermined distance from the upper film and is preferably aligned with the upper film. In order to ensure an optimal activation of the sterilising substance, all parameters, the predetermined activation temperature, the predetermined activation pressure, the predetermined activation time period and the distance of the steam nozzle to the upper film, are preferably adjusted to each other.

In the case of activation of the sterilising substance by means of evaporation after the packaging has been sealed, it is advantageous if the upper film and/or the lower part are vapour-permeable.

According to a further development of the invention, it is provided that the packaging, in particular the upper film, is evaporated with water vapour.

According to a further development of the invention, it is provided that the sterilising substance is applied to the first surface of the upper film by means of a method selected from a group consisting of spraying, pressing on, vapour deposition and rolling on. Advantageously, this ensures an optimal application of the sterilising substance to the first surface of the upper film, in particular an optimal coating of the first surface of the upper film with the sterilising substance.

According to a further development of the invention, it is provided that the closed packaging is dried for a predetermined storage time period, preferably in a vacuum chamber. Particularly preferably, the closed packaging is dried for the predetermined storage time period after activation of the sterilising substance.

According to a further development of the invention, it is provided that as sterilising substance a compound, in particular a chemical compound, selected from a group consisting of a polymer-iodine complex and a solution of diethylene glycol monoethyl ether or diethylene glycol diethyl ether with at least 40 wt % iodine to at most 50 wt % iodine, preferably 45 wt % iodine, is used. Alternatively, a mixture of substances consisting of diethylene glycol monoethyl ether or diethylene glycol diethyl ether with at least 40 wt % iodine to at most 50 wt % iodine, preferably 45 wt % iodine, is used as the sterilising substance.

According to a further development of the invention, it is provided that a transparent upper film is used as the upper film and a transparent lower part is used as the lower part. Advantageously, this enables a visual inspection of products which are arranged in the packaging.

According to a further development of the invention, it is provided that a vapour-permeable film, in particular a Tyvek® film, is used as the upper film. Advantageously, this enables a particularly favourable activation of the sterilising substance after the packaging has been closed, in particular after the upper film has been firmly bonded to the lower part.

According to a further development of the invention, it is provided that an initial germ load within the packaging is reduced by a factor of at least $10^6$. A reduction of the initial germ load by a factor of $10^6$ is also referred to as a 6-log reduction. A 6-log reduction of the initial germ load is necessary to guarantee sufficient sterilisation of the packaging.

In the context of the present technical teaching, a germ is understood to mean in particular a microorganism. Microorganisms are in particular prokaryotes, in particular bacteria and archaebacteria, eukaryotes, in particular fungi, yeasts, plant and animal unicellular and/or multicellular organisms, prions, protists, viruses and spores.

According to a further development of the invention, it is provided that a medical device is arranged within the packaging, in particular between the upper film and the lower part.

According to a further embodiment of the invention, it is provided that a pharmaceutical container is arranged within the packaging, in particular between the upper film and the lower part.

In a preferred embodiment of the method, a primary packaging means, in particular a syringe or a cartridge, is used as the medical device and/or the pharmaceutical container.

The problem is also solved by providing a packaging comprising an upper film and a lower part. The upper film and the lower part are firmly bonded and an interior of the packaging, which is delimited at least in regions by the upper film and the lower part, is sterilised by means of a method according to the invention or a method according to one or more of the embodiments described above. In connection with the packaging, the advantages already explained in connection with the method arise in particular.

In one embodiment of the packaging, the lower part is configured as a film, in particular as a plastic film. The packaging is then configured in particular as a film bag. In another embodiment, the lower part is configured as a moulded part, in particular as a moulded plastic part.

According to a further embodiment, it is provided that a medical device and/or a pharmaceutical container is arranged in the interior of the packaging, in particular between the upper film and the lower part.

The problem is also solved by providing a manufacturing device for sterilising an interior of a packaging, in particular according to a method according to the invention or a method according to one or more of the embodiments described above. The manufacturing device comprises a receiving unit, a positioning unit and an activation unit. The receiving unit is adapted to receive an upper film comprising a sterilising substance on a first surface and a lower part. The positioning unit is adapted to place the upper film on the lower part in such a way that the upper film and the lower part at least partially delimit the interior of the packaging and that the first surface of the upper film at least partially faces the interior of the packaging. The activation unit is adapted to activate the sterilising substance from the outside. In particular, the manufacturing device is adapted to perform a method according to the invention or a method according to one or more of the embodiments described above. In connection with the manufacturing device, in particular the advantages already explained in connection with the method and the packaging arise.

Preferably, the receiving unit, the positioning unit and the activation unit are arranged in such a way that the upper film and the lower part first pass through the receiving unit, then through the positioning unit and then through the activation unit.

According to a further development of the invention, it is provided that the manufacturing device comprises an application unit. The application unit is adapted to apply the sterilising substance to the first surface of the upper film.

According to a further embodiment of the invention, the manufacturing device is provided comprising a sealing unit. The sealing unit is adapted to firmly bonded the upper film and the lower part.

According to a further development of the invention, it is provided that the activation unit comprises an evaporation unit which is adapted in particular to deliver a water vapour blow out.

In order to demonstrate a sterilising effect, in particular a 6-log reduction in the initial germ load, of a method according to the invention or of a method according to one or more of the embodiments described above, the series of experiments described below were carried out.

For all experiments, a Tyvek® film was used as the upper film and a cuvette, preferably a cuvette made of polystyrene, was used as the lower part.

To demonstrate a sterilising effect, the cuvette was inoculated with *Bacillus subtilis* before the method was applied. For this purpose, a stock of *Bacillus subtilis* was grown on an agar with manganese for 3-4 weeks. Subsequently, the spores were collected with ultrapure water, especially with 2 ml ultrapure water, and washed, preferably twice. Furthermore, the presence of the spores was confirmed by observation through a microscope. Subsequently, the spores were stored in a 4% ethanol ultrapure water solution and the spore concentration was carried out by known methods, in particular a dilution series, a multiplication in a Petri dish and a counting of colony forming units, a so-called CFU counting (Colony Forming Units). For the inoculation of the cuvette, a spore suspension with more than $3\times10^9$ CFU per ml was prepared. Thus, a 6-log reduction of the initial germ load can be conclusively demonstrated, even in the case of a spontaneous reduction, typically in the range of a 1.5-log reduction, of the spores due to desiccation and/or vegetative cells still present.

Before inoculation of the cuvette with 100 µl of the spore suspension, the cuvette was sterilised with UV light. After inoculation, the cuvette was stored at 37° C. for at least 8 hours to allow the liquid to evaporate and the spores to attach to the inner walls of the cuvette.

After completion of each experiment, a CFU count was performed. In each case, 1 ml of ultrapure water was filled into the cuvette and a sterile cotton swab was used to detach the spores from the inner walls of the cuvette and dissolve them in the ultrapure water. The resulting suspension was transferred to another vessel. The process of suspension formation in the cuvette was repeated until 5 ml of the suspension had been collected in the further vessel. The 5 ml suspension was diluted in a six-step dilution series and subsamples of 1 ml each were applied to agar plates, preferably casein-soy peptone agar plates. After 24 hours and 48 hours, a CFU count was performed.

Experimental series 1: For sterilisation of the inoculated cuvette, either a solution of diethylene glycol monoethyl ether with 45 wt % iodine was pipetted onto the Tyvek® film to obtain preferably a density of 2.18 mg $I_2$ per cm², or the Tyvek® film was coated with a 1:50 iodine-ethanol solution.

The Tyvek® foil, to which iodine had previously been applied, was glued to the inoculated cuvette in such a way that the iodine solution was completely arranged within the cuvette. The cuvette and the Tyvek® foil were pressed firmly together for 30 seconds and then stored for 10 minutes to allow the adhesive bond between the cuvette and the Tyvek foil to form completely. For control experiments, a comparison cuvette inoculated in the same way was bonded to a Tyvek film to which no iodine had been applied.

Then the inoculated cuvette sealed with the Tyvek® film was treated with steam by placing a steam nozzle on the centre of the Tyvek® film, after which a blast of steam at 120° C. and a pressure of 36 psi (2.5 bar) was delivered for 5 seconds.

These respective experiments were each carried out with a plurality of cuvettes and comparison cuvettes.

The Tyvek®-sealed cuvettes and reference cuvettes were then stored at 23° C. for 72 hours before the Tyvek® was removed and a CFU count was performed. In the control experiments with the comparison cuvettes, where no iodine was discontinued onto the Tyvek® film, a 1.7-log reduction in initial germ load was observed compared to the inoculum. This 1.7-log reduction in the control experiments is based on dehydration processes. In all experiments in which iodine was applied to the Tyvek® film, no colony-forming unit was found in the CFU count. This results in at least a 6.9-log reduction in the initial germ load when sterilised by the preceding method, in particular by applying iodine to the Tyvek® film and activating the iodine by a burst of steam, compared to the control experiments.

Figure 2:
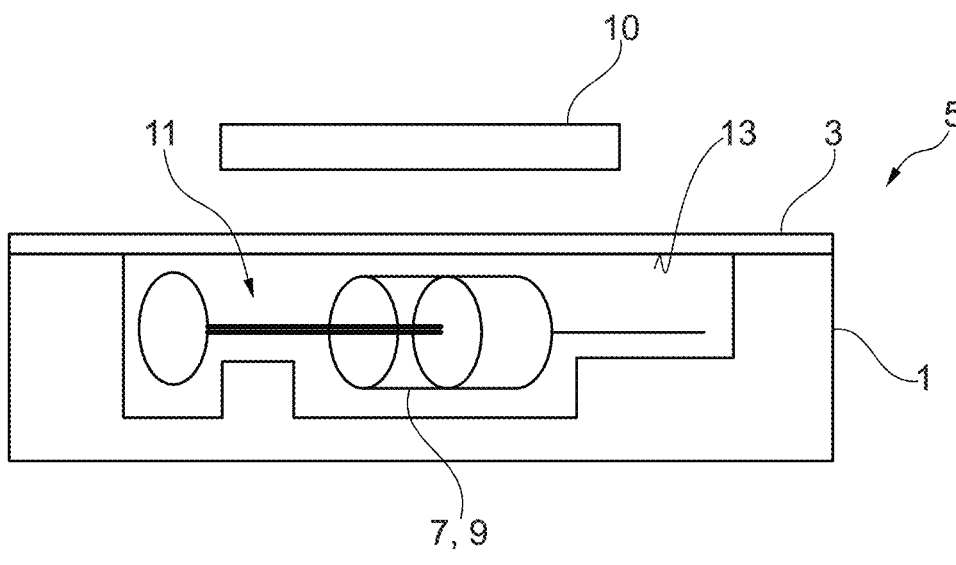

The invention is explained in more detail below with reference to the drawing. Thereby show:

FIG. 1 a schematic representation of a lower part and an upper film of a first embodiment of a packaging, FIG. 2 a schematic representation of the first embodiment of a packaging, FIG. 3 a schematic representation of a second embodiment of a packaging, FIG. 4 a schematic representation of a third embodiment of a packaging, and FIG. 5 a schematic representation of a first and a second embodiment of a manufacturing device.

FIG. 1 shows a schematic representation of a lower part 1 and an upper film 3 of a first embodiment of a packaging 5. The lower part 1 and the upper film 3 are both preferably configured to be transparent. A medical device 7 and/or a pharmaceutical container 9 is preferably arranged in the lower part 1. The upper film 3 is preferably a vapour-permeable film, in particular a Tyvek film.

In the closed state, the lower part 1 and the upper film 3 delimit an interior 11 of the packaging 5 at least in certain regions. In this case, a first surface 13 of the upper film 3 faces the interior 11 of the packaging 5 at least in certain regions.

In a method for sterilising the interior 11 of the packaging 5, in a first step a sterilising substance 15 is applied to the first surface 13 of the upper film 3, wherein the sterilising substance 15 comprises iodine. Preferably, the sterilising substance 15 comprises at least 40 wt % iodine.

Preferably, the sterilising substance 15 comprises a compound, in particular a chemical compound, selected from a group consisting of a polymer-iodine complex and a solution of diethylene glycol monoethyl ether or diethylene glycol diethyl ether having at least 40 wt % iodine to at most 50 wt % iodine, preferably 45 wt % iodine. Alternatively, a mixture of substances consisting of diethylene glycol monoethyl ether or diethylene glycol diethyl ether with at least 40 wt % iodine to at most 50 wt % iodine, preferably 45 wt % iodine, is used as the sterilising substance.

Preferably, the sterilising substance 15 is applied as a layer 17, in particular as a homogeneous layer, to the first surface 13 of the upper film 3.

Preferably, the sterilising substance 15 is applied to the first surface 13 of the upper film 3 by a method selected from a group consisting of spraying, pressing on, vapour deposition and rolling on.

Alternatively or additionally, after application to the first surface 13 of the upper film 3, the sterilising substance 15 is dried for a predetermined drying time period.

The upper film 3 is then arranged on the lower part 1 in such a way that the first surface 13 of the upper film 3 faces the interior 11 at least in certain areas.

FIG. 2 shows a schematic representation of the first embodiment of the packaging 5, which is composed of the lower part 1 and the upper film 3 from FIG. 1. In the interior 11 of the packaging 5, in particular between the lower part 1 and the upper film 3, the medical device 7 and/or the pharmaceutical container 9 is arranged.

Identical and functionally identical elements are provided with the same reference signs in all figures, so that reference is made in each case to the preceding description.

In a second step of the method for sterilising the interior 11 of the packaging 5, the sterilising substance 15 is activated externally for a predetermined activation time period.

In one embodiment of the method, the activation of the sterilising substance 15 is carried out before the packaging 5 is closed, in particular before the lower part 1 is firmly bonded to the upper film 3. Alternatively or additionally, the activation of the sterilising substance 15 is carried out after the packaging 5 has been closed, in particular after the lower part 1 has been firmly bonded to the upper film 3.

Preferably, the activation of the sterilising substance 15 is carried out by evaporation, preferably by evaporation by means of water vapour, with a predetermined activation temperature and/or a predetermined activation pressure for the predetermined activation time period.

In a preferred embodiment of the method, the packaging 5, in particular the upper film 3, is evaporated by means of a steam nozzle 10 which preferably emits water vapour.

In an optional third step of the method for sterilising the interior 11 of the packaging 5, the closed packaging 5 is dried for a predetermined storage time period. Preferably, this drying is carried out in a vacuum chamber.

In a particularly preferred embodiment of the method, the initial germ load within the packaging 5, in particular in the interior 11 of the packaging 5 and on a surface of the medical device 7 and/or a surface of the pharmaceutical container 9, is reduced by a factor of at least $10^6$.

FIG. 3 shows a schematic representation of a second embodiment of a packaging 5 with the upper film 3 and the lower part 1. The medical device 7 and/or the pharmaceutical container 9, in particular a syringe, is arranged in the interior 11 of the packaging 5. For sterilisation of the interior 11 of the packaging 5 and the surface of the medical device 7 and/or the surface of the pharmaceutical container 9, reference is made to the previous description.

FIG. 4 shows a schematic representation of a third embodiment of a packaging 5 with the upper film 3 and the lower part 1. The medical device 7 and/or the pharmaceutical container 9, in particular a syringe, is arranged in the interior 11 of the packaging 5. For sterilisation of the interior 11 of the packaging 5 and the surface of the medical device

7 and/or the surface of the pharmaceutical container 9, reference is made to the previous description.

FIG. 5 shows a schematic representation of a first and second embodiment of a manufacturing device 19.

FIG. 5 _a_) shows the first embodiment of the manufacturing device 19 for sterilising the interior 11 of a packaging 5. The manufacturing device 19 comprises a receiving unit 21, a positioning unit 23 and an activation unit 25.

The receiving unit 21 is adapted to receive an upper film 3 comprising a sterilising substance 15 on a first surface 13, and a lower part 1.

The positioning unit 23 is adapted to place the upper film 3 on the lower part 1 in such a way that the upper film 3 and the lower part 1 at least partially delimit the interior 11 of the packaging 5 and that the first surface 13 of the upper film 3 at least partially faces the interior 11 of the packaging 5.

The activation unit 25 is adapted to activate the sterilising substance 15 from the outside. Preferably, the activation device 25 comprises an evaporation unit 27 adapted in particular to deliver a water vapour blow out.

Optionally, the manufacturing device 19 comprises an application unit 29. The application unit 29 is adapted to apply the sterilising substance 15 to the first surface 13 of the upper film 3.

Optionally, the manufacturing device 19 comprises a sealing unit 31. The sealing unit 31 is adapted to firmly bond the upper film 3 and the lower part 1 after activation of the sterilising substance 15 by means of the activation device 25.

Identical and functionally identical elements are provided with the same reference signs in all figures, so that reference is made to the previous description in each case.

FIG. 5 _b_) shows the second embodiment of the manufacturing device 19 for sterilising the interior 11 of a packaging 5. Optionally, the manufacturing device 19 comprises the sealing unit 31. The sealing unit 31 is adapted to firmly bond the upper film 3 and the lower part 1 before the sterilising substance 15 is activated by means of the activation device 25.

The invention claimed is:

1. A method for sterilizing a sealed interior of a packaging,
   the packaging comprising an upper film and a lower part, wherein
   the upper film and the lower part, in a closed state of the packaging, delimit the interior at least in regions, wherein the method comprises:
   applying a sterilizing substance as a layer to a first surface of the upper film, wherein the sterilizing substance comprising iodine,
   sealing the upper film on the lower part in such a way that the first surface of the upper film faces the interior of the packaging at least in regions and the sterilizing substance is arranged inside the packaging,
   activating the sterilizing substance from an outside of the sealed packaging for a predetermined activation time period,
   wherein the activating is carried out by delivering a water vapor treatment to the packaging from a steam nozzle outside of the packaging with a predetermined activation temperature and/or a predetermined activation pressure for the predetermined activation time period.

2. The method according to claim 1, wherein the sterilizing substance comprises at least 40 wt % iodine.

3. The method according to claim 1, further comprising drying the sterilizing substance for a predetermined drying time period after application to the first surface of the upper film.

4. The method according to claim 1, further comprising activating the sterilizing substance before and after the packaging is sealed.

5. The method according to claim 1, further comprising applying the sterilizing substance to the first surface of the upper film by means of a method selected from a group consisting of spraying, pressing on, vapor deposition and rolling on.

6. The method according to claim 1, further comprising drying the closed packaging for a predetermined storage time period.

7. The method according to claim 1, further comprising using, as the sterilizing substance, a compound or mixture of substances selected from a group consisting of a polymer-iodine complex and a solution of diethylene glycol mono-ethyl ether or diethylene glycol diethyl ether with at least 40 wt % iodine to at most 50 wt % iodine.

8. The method according to claim 1, further comprising using a transparent upper film as the upper film and a transparent lower part as the lower part.

9. The method according to claim 1, further comprising using a vapour-permeable film as the upper film.

10. The method according to claim 1, further comprising arranging a medical device within the packaging.

11. The method according to claim 10, further comprising arranging the medical device between the upper film and the lower part.

12. The method according to claim 1, further comprising arranging a pharmaceutical container within the packaging.

13. The method according to claim 12, further comprising arranging the pharmaceutical container between the upper film and the lower part.

14. The method according to claim 1, wherein the predetermined activation time period is from at least 0.1 seconds to at most 300 seconds.

15. The method according to claim 1, wherein the predetermined activation temperature is about 110° C.

16. The method according to claim 1, wherein the predetermined activation pressure is about 20 psi (1.4 bar).

17. The method according to claim 1, further comprising applying the sterilizing substance as a homogeneous layer to the first surface of the upper film.

18. The method according to claim 1, further comprising vapor treating the upper film with water vapor.

19. The method according to claim 1, further comprising drying the closed packaging for a predetermined storage time period in a vacuum chamber.

20. The method according to claim 1, further comprising using a water resistant film as the upper film.

21. A manufacturing device for sterilizing a sealed interior of a packaging, wherein the manufacturing device comprising an application unit, a receiving unit, a positioning unit, a sealing unit, and an activation unit, wherein the receiving unit is adapted to receive an upper film with a first surface and a lower part, wherein the positioning unit is adapted to place the upper film on the lower part in such a way that the upper film and the lower part delimit the interior of the packaging at least in regions and that the first surface of the upper film faces the interior of the packaging at least in regions and a sterilizing substance is arranged inside the packaging, wherein the sealing unit is adapted to seal the upper film on the lower part, wherein the activation unit comprises an evaporation unit, wherein the activation unit is adapted to activate a sterilizing substance applied on the first surface from an outside by delivering a water vapor treatment to the sealed packaging from a steam nozzle outside of the packaging with a predetermined activation temperature and/or a predetermined activation pressure for a predetermined activation time period, and wherein the application unit is adapted to apply the sterilizing substance to the first surface as a layer to the first surface of the upper film.

22. The manufacturing device according to claim 21, wherein the evaporation unit is adapted to deliver a water vapor blow out.

* * * * *